United States Patent
Kim et al.

(10) Patent No.: US 10,281,395 B2
(45) Date of Patent: May 7, 2019

(54) APPARATUS AND METHOD FOR MEASURING DUST

(71) Applicant: LG ELECTRONICS INC., Seoul (KR)

(72) Inventors: Bolam Kim, Seoul (KR); Seonghong Park, Seoul (KR); Sangkeun Lee, Seoul (KR); Pilwon Jeong, Seoul (KR); Yongho Cho, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/625,825

(22) Filed: Jun. 16, 2017

(65) Prior Publication Data

US 2018/0011018 A1 Jan. 11, 2018

(30) Foreign Application Priority Data

Jun. 16, 2016 (KR) .................. 10-2016-0075344

(51) Int. Cl.
*G01N 21/53* (2006.01)
*G01N 21/47* (2006.01)

(52) U.S. Cl.
CPC ....... *G01N 21/53* (2013.01); *G01N 2021/473* (2013.01); *G01N 2021/4711* (2013.01)

(58) Field of Classification Search
CPC .................. G01N 21/53; G01N 15/06; G01N 2015/0693; G01N 2021/473;

(Continued)

(56) References Cited

U.S. PATENT DOCUMENTS

| 8,040,508 B2 | 10/2011 | Holve |
| 2004/0188598 A1* | 9/2004 | Kawai .................. G01N 21/53 250/222.2 |

(Continued)

FOREIGN PATENT DOCUMENTS

| JP | 2000146814 | 5/2000 |
| JP | 2013109751 | 6/2013 |

OTHER PUBLICATIONS

PCT International Application No. PCT/KR2017/005587, Notification of Transmittal of the International Search Report and the Written Opinion of the International Searching Authority, or Declaration dated Aug. 30, 2017, 14 pages.

*Primary Examiner* — Isiaka O Akanbi
(74) *Attorney, Agent, or Firm* — Lee, Hong, Degerman, Kang & Waimey

(57) ABSTRACT

Disclosed herein is a dust measuring apparatus and method for measuring a dust concentration in a flow channel. The apparatus includes a flow channel unit for defining a flow channel allowing a fluid containing dust to move therethrough, a light emitter for emitting light into the flow channel, a light detector for detecting light scattered from the dust in the flow channel and converting it to an electrical detection signal, the light detector including a plurality of detectors having different light detection ranges, and a controller for controlling the flow channel unit, the light emitter and the light detector, wherein the controller is configured to receive detection signals from the detectors, compensate for an offset for the received detection signals, and measure a dust concentration based on the compensated detection signals.

18 Claims, 12 Drawing Sheets

(58) Field of Classification Search
CPC .......... G01N 15/0211; G01N 15/1459; G01N 2201/12; G01N 2015/1493; G01N 2201/068; G01N 2201/06113; G01N 21/0303; G01N 2015/1497
USPC .............. 356/335–336, 343, 338, 438–9
See application file for complete search history.

(56) References Cited

U.S. PATENT DOCUMENTS

| | | |
|---|---|---|
| 2012/0050737 A1 | 3/2012 | Dowaki et al. |
| 2012/0154172 A1* | 6/2012 | O'Hara ............ H04Q 9/00 340/870.02 |
| 2014/0152986 A1 | 6/2014 | Trainer |

* cited by examiner

APPARATUS AND METHOD FOR MEASURING DUST

Pursuant to 35 U.S.C. § 119(a), this application claims the benefit of earlier filing date and right of priority to Korean Patent Application No. 10-2016-0075344, filed on Jun. 16, 2016, the contents of which are all hereby incorporated by reference herein in its entirety.

BACKGROUND OF THE INVENTION

Field of the Invention

The present invention relates to a dust measuring apparatus and method for measuring a dust concentration in a flow channel.

Discussion of the Related Art

Recently, the frequency of exposure to fine dust emitted from automobiles and factories has increased and the hazard of fine dust to human bodies is well known.

Given these circumstances, various apparatuses for measuring fine dust have been developed with increase of interest in health.

A dust measuring apparatus may include a light emitter for emitting light, a flow channel defining unit for defining a flow channel through which dust passes, and a light detector for detecting light scattered by the dust. The dust measuring apparatus may detect dust only when the dust is present in a common region shared by a flow channel region, a light emission region and a light detection region.

Accordingly, the volume of the common region is one of factors that may affect the dust measuring apparatus in relation to precision of detection of dust concentrations.

However, the conventional dust measuring apparatus consists of one light module and one detection module, and accordingly the measurement precision thereof for low-concentration dust or high-concentration dust may be limited by the configuration of the light detection module.

That is, if the detection region of the light detection module is small, the probability of presence of dust in the detection region is low, and thus measurement precision for low-concentration dust may be lowered.

If the detection region of the light detection module is large, measurement precision for low-concentration dust may be improved, but measurement precision for high-concentration dust may be lowered.

Accordingly, there is a need for a dust measuring apparatus capable of enhancing measurement precision for both low-concentration dust and high-concentration dust by widening the detection region.

SUMMARY OF THE INVENTION

An object of the present invention is to solve the above and other problems. Another object of the present invention is to provide an apparatus and method for measuring dust which may widen a dust measurement range using multiple detectors having different light detection ranges.

Another object of the present invention is to provide an apparatus and method for measuring dust which may enhance measurement precision in a wide measurement range by compensating for an offset for detection signals received from multiple detectors.

Another object of the present invention is to provide an apparatus and method for measuring dust which may have a simple design structure as a light detection range of a detector is determined using lenses having different angles of view.

Another object of the present invention is to provide an apparatus and method for measuring dust which may reduce the overall size of the apparatus by implementing efficient spatial arrangement by disposing a detector having a wider measurement range adjacent to a light emitter.

Another object of the present invention is to provide an apparatus and method for measuring dust which may enhance dust measurement precision by arranging detectors such that the central axes of the detectors intersect each other in the light emission region of a flow channel.

Another object of the present invention is to provide an apparatus and method for measuring dust which may determine the light detection range of a detector by adjusting the distance between the optical axis of the light emitter and the detector.

Another object of the present invention is to provide an apparatus and method for measuring dust which may reduce optical noise by arranging a light absorber in a region facing a light emitter or detector.

Another object of the present invention is to provide an apparatus and method for measuring dust which may compensate for an offset of detection signals based on the offset calculated by comparing the detection signals with a predetermined reference value.

Another object of the present invention is to provide an apparatus and method for measuring dust which may compensate for an offset of detection signals by dividing the detection signals into a low-concentration section, a discontinuous section and a high-concentration section according to dust concentrations and adjusting weights for some detection signals.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an apparatus for measuring dust includes a flow channel defining unit for defining a flow channel allowing a fluid containing dust to move therethrough, a light emitter for emitting light into the flow channel, a light detector for detecting light scattered from the dust in the flow channel and converting the same into an electrical detection signal, the light detector including a plurality of detectors having different light detection ranges, and a controller for controlling the flow channel defining unit, the light emitter and the light detector, wherein the controller is configured to receive detection signals from the detectors, compensate for an offset for the received detection signals, and measure a dust concentration based on the compensated detection signals.

In another aspect of the present invention, there is provided a method for measuring dust including receiving detection signals from the detectors, compensating for an offset for the received detection signals, and measuring a dust concentration based on the compensated detection signals.

It is to be understood that both the foregoing general description and the following detailed description of the present invention are exemplary and explanatory and are intended to provide further explanation of the invention as claimed.

BRIEF DESCRIPTION OF THE DRAWINGS

Arrangements and embodiments will be described in detail with reference to the following drawings in which like reference numerals refer to like elements and wherein.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts. As used herein, the suffixes "module" and "unit" are added or used interchangeably simply to facilitate preparation of this specification and are not intended to suggest unique meanings or functions. In describing embodiments disclosed in this specification, relevant well-known technologies may not be described in detail in order not to obscure the subject matter of the present invention. In addition, the accompanying drawings are merely intended to facilitate understanding of the embodiments disclosed in this specification and not to restrict the technical spirit of the present invention. In addition, the accompanying drawings should be understood as covering all equivalents or substitutions within the scope of the present invention.

Terms including ordinal numbers such as first, second, etc. may be used to explain various elements. However, it will be appreciated that the elements are not limited to such terms. These terms are merely used to distinguish one element from another.

When one constituent is said to be "connected" or "linked" to another, it should be understood that this means that the one constituent may be directly connected or linked to another one or another constituent may be interposed between the constituents. On the other hand, when one constituent is said to be "directly connected" or "directly linked" to another, it should be understood that this means no other constituent is interposed between the constituents.

Singular nouns encompass the plural forms thereof unless context clearly indicates otherwise.

Terms used in this specification are merely adopted to explain specific embodiments, and are not intended to limit the present invention. A singular expression includes a plural expression unless the two expressions are contextually different from each other. In this specification, terms such as "includes" or "has" are intended to indicate that characteristics, figures, steps, operations, constituents, and components disclosed in the specification or combinations thereof exist. The terms "includes" or "has" should be understood as not precluding possibility of existence or addition of one or more other characteristics, figures, steps, operations, constituents, components, or combinations thereof.

Figure 1:
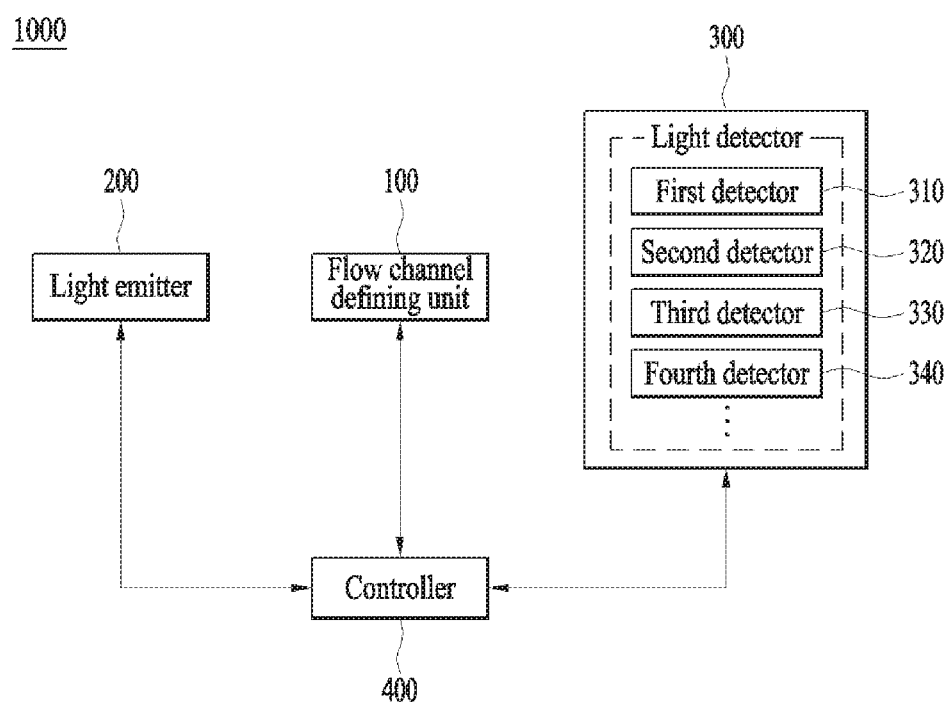
FIG. 1 is a block diagram illustrating a dust measuring apparatus according to an embodiment of the present invention.

FIG. 1 is a block diagram illustrating a dust measuring apparatus according to an embodiment of the present invention.

As shown in FIG. 1, a dust measuring apparatus 1000 may include a flow channel defining unit 100, a light emitter 200, a light detector 300, and a controller 400.

The flow channel defining unit 100 may define a flow channel through which a fluid containing dust moves. Herein, the flow channel defining unit 100 may be disposed at various positions in the apparatus where the flow channel may be defined. In addition, the flow channel defining unit 100 may form a negative pressure in the flow channel, and adjust the magnitude of the negative pressure according to the control signal of the controller 400 to control the movement speed of the fluid.

Next, the light emitter 200 may emit light into the flow channel. The light emitter 200 may be disposed at one side of the flow channel, and include a laser diode for emitting laser light. Herein, the light emitted into the flow channel may be scattered through interaction with dust particles in the flow channel.

In one embodiment, the light emitter 200 may include a diffusion lens for diffusing light. Herein, the diffusion lens serves to diffuse light such that the plurality of light detectors having different light detection ranges may accurately detect light.

In another embodiment, the light emitter 200 may include a light absorber. The light absorber may be disposed to face the light emitter 200, and absorb light emitted from the light emitter 200. Herein, the reason for disposing the light absorber is that reflected light may be produced in the apparatus by reflection of light emitted from the light emitter 200, and function as noise in the light detector, thereby lowering reliability of a detection signal of the light detector.

Next, the light detector 300 may detect light scattered by the dust in the flow channel, and convert the same into an electrical detection signal. Herein, the light detector 300 may be configured by a plurality of detectors having different light detection ranges. For example, the light detector 300 may include a first detector 310, a second detector 320, a third detector 330, and a fourth detector 340.

For example, the plurality of detectors may include a first detector for detecting light scattered within a first detection range in the light emission region of the flow channel and a second detector for detecting light scattered within a second detection range in the light emission region of the flow channel, the second detection range being narrower than the first detection range. The first detector may include a first lens having a first angle of view, and the second detector may include a second lens having a second angle of view, which is narrower than the first angle of view. In addition, the first detector may be disposed at a first distance from the central axis of the light emitted from the light emitter 200, and the second detector may be disposed at a second distance from the central axis of the light emitted from the light emitter 200. The first distance may be equal to the second distance. In addition, the first detector and the second detector may be disposed such that the central axis of the first detector and the central axis of the second detector intersect each other in the light emission region of the flow channel. Herein, the point at which the central axis of the first detector and the central axis of the second detector intersect each other may be a point which the central axis of light emitted from the light emitter 200 crosses in the light emission region of the flow channel.

In one embodiment, the first and second detectors may be disposed at one side of the central axis of light emitted from the light emitter 200. Herein, the first detector may be disposed such that the central axis of the first detector and the central axis of light emitted from the light emitter 200 form a first angle therebetween, and the second detector may be disposed such that the central axis of the second detector and the central axis of light emitted from the light emitter 200 form a second angle therebetween. The first angle may be less than the second angle. In addition, the first and second detectors may be positioned in the same plane as the light emitter 200, or may be positioned in a plane different from the plane in which the light emitter 200 is positioned.

In another embodiment, the first detector may be disposed at one side of the central axis of light emitted from the light emitter 200, and the second detector may be disposed at the opposite side of the central axis of the light emitted from the light emitter 200. Herein, the first and second detectors may be disposed symmetrically with respect to the central axis of light emitted from the light emitter 200. In addition, the first detector may be disposed such that the central axis of the first detector and the central axis of light emitted from the light emitter 200 form a first angle therebetween, and the second detector may be disposed such that the central axis of the second detector and the central axis of light emitted from the light emitter 200 form a second angle therebetween. The first angle may be equal to the second angle. Herein, the first and second detectors may be positioned in the same plane as the light emitter 200, or may be positioned in a plane different from the plane in which the light emitter 200 is positioned.

As another example, the first detector may include a first lens having a first angle of view, and the second detector may include a second lens having a second angle of view, which may be equal to the first angle of view. Herein, the first detector may be disposed at a first distance from the central axis of the light emitted from the light emitter 200, and the second detector may be disposed at a second distance from the central axis of the light emitted from the light emitter 200. The first distance may be shorter than the second distance. In addition, the first detector and the second detector may be disposed such that the central axis of the first detector and the central axis of the second detector intersect each other in the light emission region of the flow channel. Herein, the point at which the central axis of the first detector and the central axis of the second detector intersect each other may be a point which the central axis of the light emitted from the light emitter 200 crosses in the light emission region of the flow channel.

In one embodiment, the first and second detectors may be disposed at one side of the central axis of light emitted from the light emitter 200. Herein, the first detector may be disposed such that the central axis of the first detector and the central axis of light emitted from the light emitter 200 form a first angle therebetween, and the second detector may be disposed such that the central axis of the second detector and the central axis of light emitted from the light emitter 200 form a second angle therebetween. The first angle may be less than the second angle. In addition, the first and second detectors may be positioned in the same plane as the light emitter 200, or may be positioned in a plane different from the plane in which the light emitter 200 is positioned.

In another embodiment, the first detector may be disposed at one side of the central axis of light emitted from the light emitter 200, and the second detector may be disposed at the opposite side of the central axis of the light emitted from the light emitter 200. Herein, the first and second detectors may be disposed symmetrically with respect to the central axis of light emitted from the light emitter 200. In addition, the first detector may be disposed such that the central axis of the first detector and the central axis of light emitted from the light emitter 200 form a first angle therebetween, and the second detector may be disposed such that the central axis of the second detector and the central axis of light emitted from the light emitter 200 form a second angle therebetween. The first angle may be equal to the second angle. The first and second detectors may be positioned in the same plane as the light emitter 200, or may be positioned in a plane different from the plane in which the light emitter 200 is positioned.

The first detector may be disposed adjacent to the light emitter 200, and the second detector may be disposed far from the light emitter 200. Since the emission range of light emitted from the light emitter 200 is widened with increasing distance from the light emitter 200, efficient light detection may be implemented if the second detector, which has a narrower light detection range than the first detector, is disposed at a longer distance from the light emitter 200 than the first detector.

In addition, the first and second detectors may be disposed around the path of light emitted from the light emitter 200. If the first and second detectors are positioned in the path of light, not only scattering light but also optical noise may be detected. Accordingly, the first and second detectors should be disposed not to partially or fully overlap the path of light.

The first and second detectors may include a light absorber disposed to face the detectors. Herein, the light absorber may be disposed to face the corresponding detector across the central axis of light emitted from the light emitter 200, and absorb light scattered by the dust in the flow channel. The light absorber may be disposed in one-to-one correspondence with multiple detectors. The light absorber is disposed as above because the scattering light scattered by the dust functions as noise in the detector, lowering reliability of the detection signal of the detector.

The controller 400 may control the flow channel defining unit 100, the light emitter 200, and the light detector 300. The controller 400 may receive detection signals from multiple detectors, compensate for an offset for the detection signals, and measure a dust concentration based on a compensated detection signal.

In compensating for the offset for the received detection signals, the controller 400 may calculate an offset by comparing the detection signals with a predetermined reference value, and compensate for the offset of the detection signals based on the calculated offset.

For example, the controller 400 may include an offset compensator for compensating for an offset for received detection signals. The offset compensator may include a calculator for calculating an offset value by comparing the detection values received from multiple light detectors with a predetermined reference value and a compensator for compensating for the offset of the detection values based on the calculated offset value and outputting a compensated detection value to the calculator.

As another example, in compensating for the offset for the received detection signals, the controller 400 may divide the detection signals into a low-concentration section, a discontinuous section and a high-concentration section according to dust concentrations. The controller 400 may reflect, in the low-concentration section, a first detection signal received from a detector having a first light detection range, and reflect, in the high-concentration section, a second detection signal received from a detector having a second light detection range, which is narrower than the first light detection range. In the discontinuous section, the controller 400 may reflect a third detection signal, which is obtained by increasing the reflection weight of the first detection signal and decreasing the reflection weight of the second detection signal as a concentration point moves toward the low-concentration section in by decreasing the reflection weight of the first detection signal and increasing the reflection weight of the second detection signal as a concentration point moves toward the high-concentration section.

As another example, in compensating for the offset for the received detection signals, the controller 400 may divide the detection signals into a low-concentration section, a discontinuous section and a high-concentration section according to dust concentrations. In the low-concentration section, the offset of the detection signals may be compensated for according to Equation 1 below. In the high-concentration section, the offset of the detection signals may be compensated for according to Equation 2 below. In the discontinuous section, the offset of the detection signals may be compensated for according to Equation 3 below.

$Co=Cw$ (wherein Co denotes a compensated detection signal, and Cw denotes the first detection signal received from a detector having a wide light detection range)    Equation 1

$Co=Cn$ (wherein Co denotes a compensated detection signal, and Cn denotes the second detection signal received from a detector having a narrow light detection range)    Equation 2

$Wn$=Update $Wn(Co)$ $Co=Cn*Wn+Cw*(1-Wn)$    Equation 3

(wherein Wn denotes a reflection weight (between 0 and 1) of the second detection signal received from a detector having a narrow light detection range)

As another example, in compensating for the offset for the received detection signals, the controller 400 may calculate an offset by comparing the detection signals with a predetermined reference value, and perform primary compensation for the offset of the detection signals based on the calculated offset. Then, the controller 400 may arrange a low-concentration section, a discontinuous section and a high-concentration section according to dust concentrations from the detection signals for which the primary compensation for the offset has been performed. The controller 400 may consider a first detection signal received from a detector having a first light detection range in the low-concentration section, and consider, in the high-concentration section, a second detection signal received from a detector having a second light detection range, which is narrower than the first light detection range. In the discontinuous section, the controller 400 may consider a third detection signal obtained by differently adjusting the weight of the first detection signal according to the sections. Thereby, the controller 400 may perform secondary compensation for the offset of the detection signals. Herein, in the discontinuous section, the third detection signal may be obtained by increasing the weight of the first detection signal and decreasing the weight of the second detection signal as a concentration point moves toward the low-concentration section and by decreasing the weight of the first detection signal and increasing the weight of the second detection signal as the concentration point moves toward the high-concentration section.

According to an embodiment of the present invention, the dust measurement range may be widened using multiple detectors having different light detection ranges as described above.

In addition, measurement precision may be enhanced in a wide measurement range by compensating for the offset for detection signals received from multiple detectors. In addition, the light detection ranges of the detectors are determined using lenses having different angles of view. Accordingly, a simple and low-cost design may be implemented.

In addition, according to an embodiment of the present invention, the overall size of the apparatus may be reduced through efficient spatial arrangement, by arranging a detector having a wider measurement range adjacent to the light emitter. Further, the detectors may be disposed such that the central axes of the detectors intersect each other in the light emission region of the flow channel. Thereby, precision of dust measurement may be enhanced.

In addition, according to an embodiment of the present invention, the light detection range of a detector may be easily and simply determined by adjusting the distance between the optical axis of the light emitter and the detector. In addition, as a light absorber is disposed in a region facing the light emitter or the detector, optical noise may be reduced.

In addition, according to an embodiment of the present invention, an offset may be calculated by comparing detection signals with a predetermined reference value, and the offset of detection signals may be easily and simply compensated for based on the calculated offset.

In addition, according to an embodiment of the present invention, detection signals may be divided into a low-concentration section, a discontinuous section and a high-concentration section according to dust concentrations and the offset of the detection signals is compensated for by adjusting weights for some detection signals according to the sections. Accordingly, reliability of compensation may be enhanced.

Figure 2:
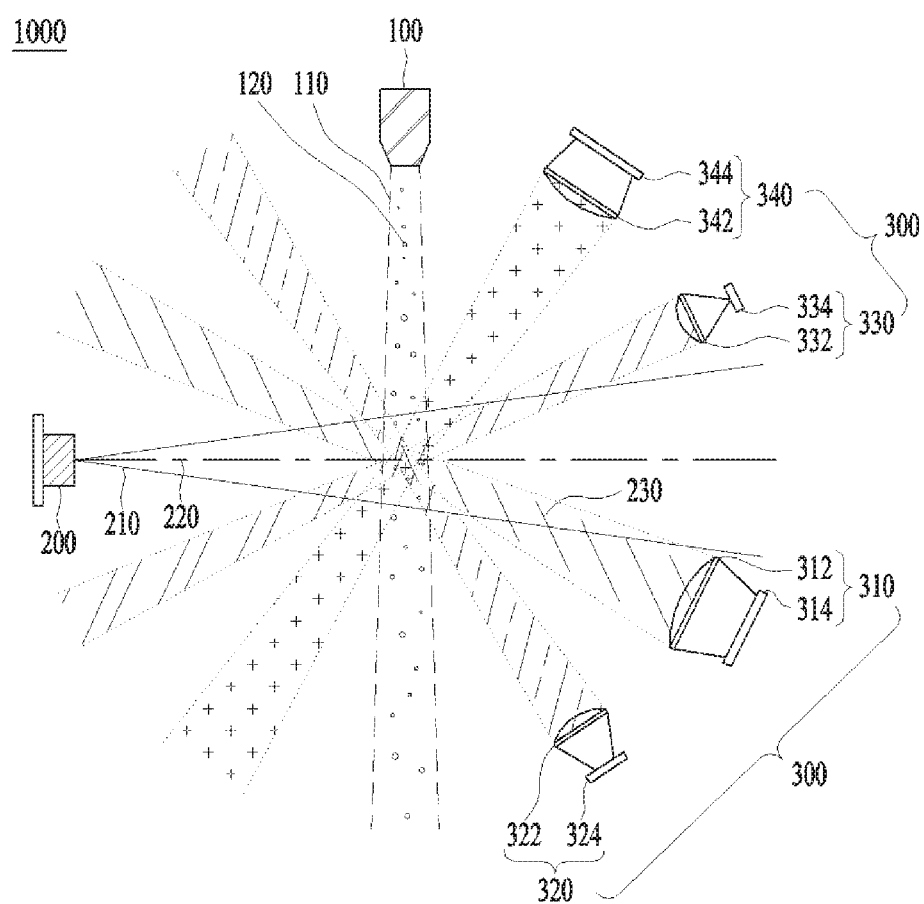
FIG. 2 illustrates arrangement of the light detector of FIG. 1.

FIG. 2 illustrates arrangement of the light detector of FIG. 1.

As shown in FIG. 2, the dust measuring apparatus 1000 may include a flow channel defining unit 100, a light emitter 200, and a light detector 300.

The flow channel defining unit 100 may define a flow channel 110 through which a fluid containing dust particles 120 moves.

The light emitter 200 may emit light 210 into the flow channel 110. Herein, the light 210 emitted into the flow channel 110 may be scattered through interaction with the dust particles 120 in the flow channel 110.

The light detector 300 may detect scattering light 230 scattered by the dust particles 120 in the flow channel 110 and convert the same into an electrical detection signal. The light detector 300 may include a plurality of detectors having different light detection ranges. For example, the light detector 300 may include a first detector 310, a second detector 320, a third detector 330, and a fourth detector 340.

The first detector 310 may detect the scattering light 230 scattered within a first detection range in the light emission region of the flow channel 110, and the second detector 320 may detect the scattering light 230 scattered within a second detection range in the light emission region of the flow channel 110. The third detector 330 may detect the scattering light 230 scattered within a third detection range in the light emission region of the flow channel 110, and the fourth detector 340 may detect the scattering light 230 scattered within a four detection range in the light emission region of the flow channel 110. Among the detection ranges, the first detection range of the first detector 310 may be the widest, and the third detection range of the third detector 330 may be the narrowest. In addition, the fourth detection range of the fourth light detector 340 is narrower than the first detection range of the first light detector 310 and wider than the third detection range of the third light detector 330, and the second detection range of the second light detector 320 is narrower than the fourth detection range of the fourth light detector 340 and wider than the third detection range of the third light detector 330.

In addition, the first detector 310 may include a first lens 312 having a first angle of view and a first sensor 314, and the second detector 320 may include a second lens 322 having a second angle of view and a second sensor 324. The third detector 330 may include a third lens 332 having a third angle of view and a third sensor 334, and the fourth detector 340 may include a fourth lens 342 having a fourth angle of view and a fourth sensor 344. Among the angles of view, the first angle of view of the first lens 312 of the first detector 310 may be the widest, and the third detection range of the third lens 332 of the third detector 330 may be the narrowest. In addition, the fourth angle of view of the fourth lens 342 of the fourth light detector 340 is narrower than the first angle of view of the first lens 312 of the first light detector 310 and wider than the third angle of view of the third lens 332 of the third light detector 330, and the second angle of view of the second lens 322 of the second light detector 320 is narrower than the fourth angle of view of the fourth lens 342 of the fourth light detector 340 and wider than the third angle of view of the third lens 332 of the third light detector 330.

The first light detector 310, the second light detector 320, the third light detector 330, and the fourth light detector 340 may be disposed at the same distance from the central axis 220 of light 210 emitted from the light emitter 200. Herein, the angles of view of the lenses of the first light detector 310, the second light detector 320, the third light detector 330 and the fourth light detector 340 may be different from each other.

In one embodiment, the first light detector 310, the second light detector 320, the third light detector 330, and the fourth light detector 340 may be disposed at different distances from the central axis 220 of light 210 emitted from the light emitter 200. Herein, the angles of view of the lenses of the first light detector 310, the second light detector 320, the third light detector 330 and the fourth light detector 340 may be the same.

Next, the first light detector 310, the second light detector 320, the third light detector 330 and the fourth light detector 340 may be disposed such that the central axes thereof intersect each other in the light emission region of the (110). Herein, the point at which the central axes of the first light detector 310, the second light detector 320, the third light detector 330 and the fourth light detector 340 intersect each other may be a point which the central axis of light 210 emitted from the light emitter 200 crosses in the light emission region of the flow channel.

In addition, the first light detector 310, the second light detector 320, the third light detector 330 and the fourth light detector 340 may be positioned in the same plane as the light emitter 200.

Alternatively, the first light detector 310, the second light detector 320, the third light detector 330 and the fourth light detector 340 may be disposed in a plane different from the plane in which the light emitter 200 is positioned.

As described above, with the present invention, the dust measurement range may be widened using multiple detectors have different light detection ranges.

Figure 3:
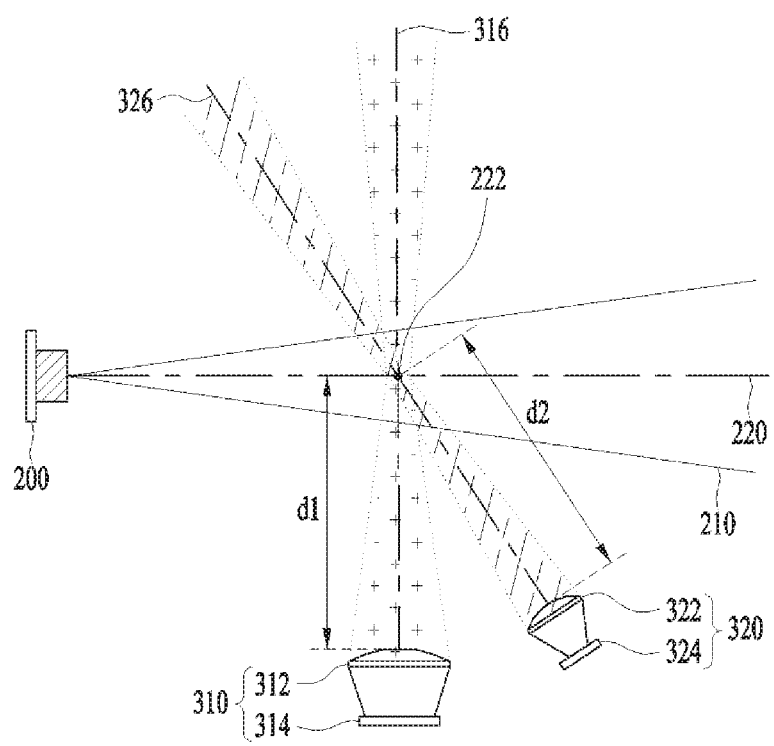
FIGS. 3 to 5 illustrate a dust measuring apparatus according to an embodiment of the present invention.
Figure 4:
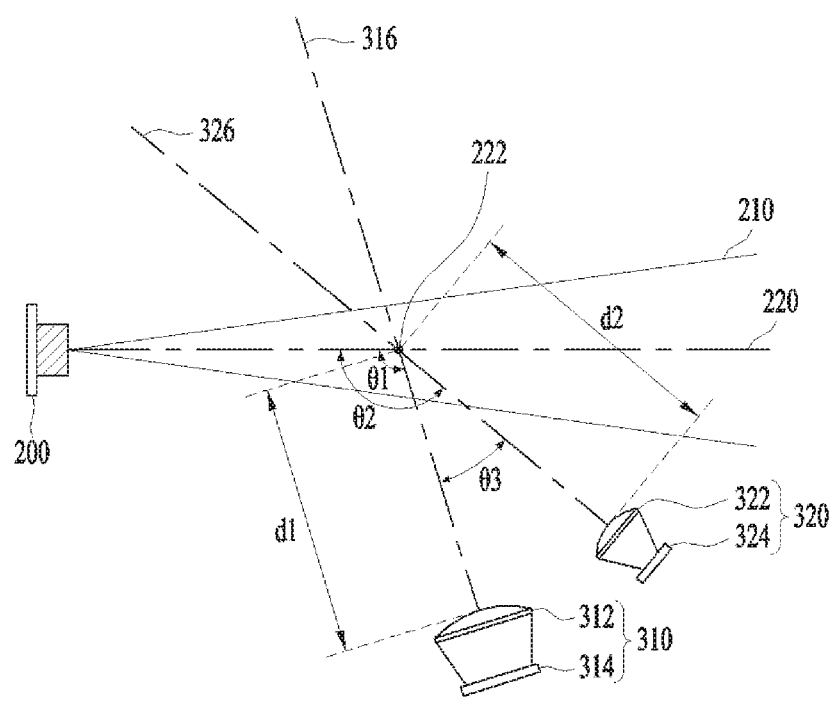
Figure 5:
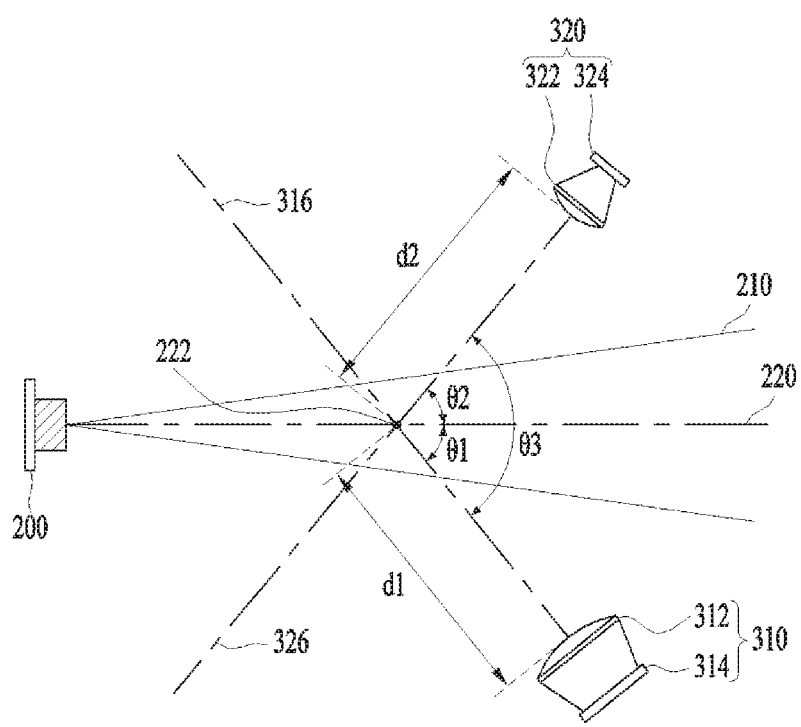

FIGS. 3 to 5 illustrate a dust measuring apparatus according to an embodiment of the present invention.

As shown in FIG. 3, the light emitter 200 may include a light detector 300. The light detector 300 may include a plurality of detectors. For simplicity, only two detectors will be described.

For example, the light detector 300 may include a first detector 310 for detecting light scattered within a first detection range in the light emission region of a flow channel and a second detector 320 for detecting light scattered within a second detection range narrower than the first detection range in the light emission region of the flow channel.

In addition, the first detector 310 may include a first lens 312 having a first angle of view and a first sensor 314, and the second detector 320 may include a second lens 322 having a second angle of view which is narrower than the first angle of view and a second sensor 324. Herein, the first sensor 314 of the first light detector 310 may detect incident light from the first lens 312 and convert the same into an electrical detection signal, and the second sensor 324 of the second light detector 320 may detect incident light from the second lens 322 and convert the same into an electrical detection signal.

The first light detector 310 may be disposed at a first distance d1 from the central axis 220 of light 210 emitted from the light emitter 200, and the second light detector 320 may be disposed at a second distance d2 from the central axis 220 of light 210 emitted from the light emitter 200. The first distance d1 may be equal to the second distance d2. In addition, the first detector 310 and the second detector 320 may be disposed such that the central axis 316 of the first detector 310 and the central axis 326 of the second detector 320 intersect each other in the light emission region of the flow channel. Herein, the point at which central axis 316 of the first detector 310 and the central axis 326 of the second detector 320 intersect each other may be a point which the central axis 220 of the light 210 emitted from the light emitter 200 crosses in the light emission region of the flow channel.

As the first and second detectors 310 and 320 having different light detection ranges are arranged, the dust measurement range may be widened, and dust ranging from low-concentration dust to high-concentration dust may be precisely and accurately measured.

As shown in FIG. 4, the first and second detectors 310 and 320 may be disposed at one side of the central axis 220 of light 210 emitted from the light emitter 200.

The first detector 310 may be disposed such that the central axis 316 of the first detector 310 and the central axis 220 of light 210 emitted from the light emitter 200 form a first angle θ1 therebetween, and the second detector 320 may be disposed such that the central axis 326 of the second detector 320 and the central axis 220 of light 210 emitted from the light emitter 200 form a second angle θ2 therebetween. Herein, the first angle θ1 may be less than the second angle θ2. Since the emission range of light 210 emitted from the light emitter 200 is widened with increase of the distance from the light emitter 200, efficient light detection may be implemented if the second detector 320, which has a narrower light detection range than the first detector 310, is disposed at a longer distance from the light emitter 200 than the first detector 310. The first angle θ1 and the second angle θ2 may be between, for example, about 45° and about 135°. However, embodiments of the present invention are not limited thereto.

In addition, the first and second detectors 310 and 320 may be disposed such that the central axis 316 of the first light detector 310 and the central axis 326 of the second light detector 320 form a third angle θ3 which is an acute angle.

If the third angle θ3 between the central axis 316 of the first light detector 310 and the central axis 326 of the second light detector 320 is greater than the acute angle, the space for arrangement of the first and second detectors 310 and 320 may become large and improper to implement compact design of the apparatus.

Accordingly, the first light detector 310 having a wide light detection range is preferably disposed adjacent to the light emitter 200, and the second light detector 320 having a narrow light detection range is preferably disposed far from the light emitter 200.

The first and second detectors 310 and 320 may be positioned in the same plane as the light emitter 200, or may be positioned in a plane different from the plane in which the light emitter 200 is positioned.

As such, according to an embodiment of the present invention, the first and second detectors 310 and 320 may be disposed in various ways to reduce the space for arrangement thereof.

As shown in FIG. 5, the first light detector 310 may be disposed at one side of the central axis 220 of light 210 emitted from the light emitter 200, and the second detector 320 may be disposed at the opposite side of the central axis 220 of light 210 emitted from the light emitter 200. Herein, the first and second detectors 310 and 320 may be disposed symmetrically with respect to the central axis 220 of light 210 emitted from the light emitter 200.

In addition, the first detector 310 may be disposed such that the central axis 316 of the first detector 310 and the central axis 220 of light 210 emitted from the light emitter 200 form a first angle θ1 therebetween, and the second detector 320 may be disposed such that the central axis 326 of the second detector 320 and the central axis 220 of light 210 emitted from the light emitter 200 form a second angle θ2 therebetween. Herein, the first angle θ1 may be equal to the second angle θ2. The first angle θ1 and the second angle θ2 may be between, for example, about 45° and about 135°. However, embodiments of the present invention are not limited thereto.

If the first and second detectors 310 and 320 are symmetrically disposed as described above, the space for arrangement of the first and second detectors 310 and 320 becomes large, and thus does not overlap the path of light emitted from the light emitter 200. Accordingly, optical noise may not be detected and, thus measurement precision and reliability may be improved.

The first and second detectors 310 and 320 may be disposed such that the central axis 316 of the first light detector 310 and the central axis 326 of the second light detector 320 form a third angle θ3 which is an obtuse angle therebetween. If the third angle θ3 between the central axis 316 of the first light detector 310 and the central axis 326 of the second light detector 320 is less than the obtuse angle, the first and second detectors 310 and 320 may partially or fully overlap the path of light from the light emitter 200, and thus optical noise may be detected. Thereby, measurement precision and reliability may be lowered.

The first and second detectors 310 and 320 may be positioned in the same plane as the light emitter 200, or may be positioned in a plane different from the plane in which the light emitter 200 is positioned.

As such, according to embodiments of the present invention, the first and second detectors 310 and 320 may be disposed in various ways such that optical noise is not detected.

Since the light detection ranges of the detector are determined using lenses having different angles of view, a simple and low-cost design may be implemented.

In addition, according to an embodiment of the present invention, the overall size may be reduced through efficient spatial arrangement, by arranging a detector having a wider measurement range adjacent to the light emitter.

Figure 6:
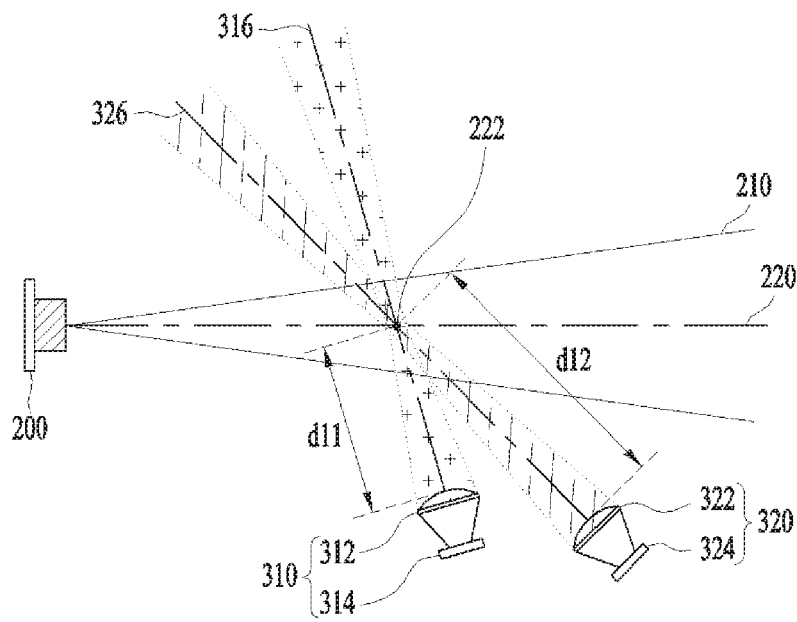
FIGS. 6 to 8 illustrate a dust measuring apparatus according to another embodiment of the present invention.
Figure 7:
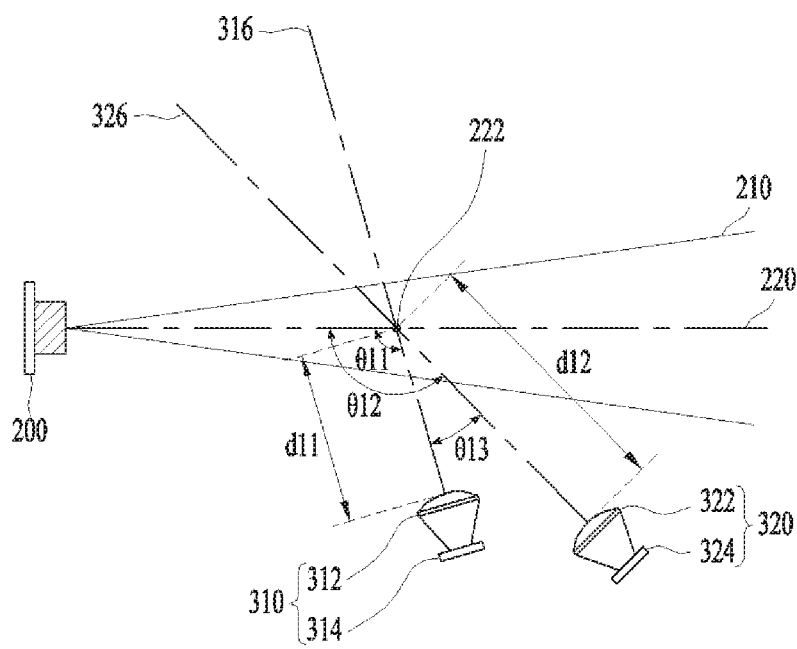
Figure 8:
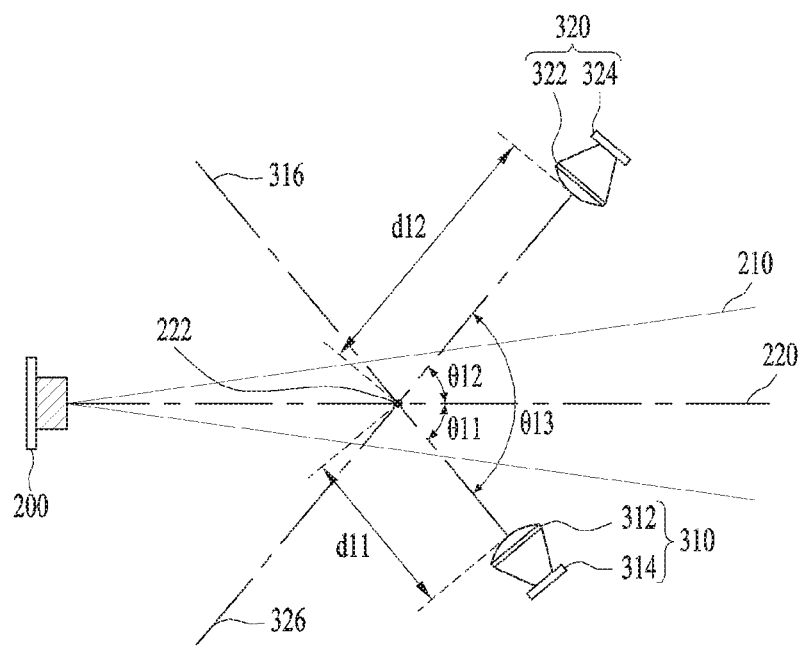

FIGS. 6 to 8 illustrate a dust measuring apparatus according to another embodiment of the present invention.

As shown in FIG. 6, the dust measuring apparatus according to this embodiment may include a light emitter 200 and a light detector 300. The light detector 300 may include a plurality of detectors. For simplicity, only two detectors will be described.

For example, the light detector 300 may include a first detector 310 for detecting light scattered within a first detection range in the light emission region of a flow channel and a second detector 320 for detecting light scattered within a second detection range narrower than the first detection range in the light emission region of the flow channel.

In addition, the first detector 310 may include a first lens 312 having a first angle of view and a first sensor 314, and the second detector 320 may include a second lens 322 having a second angle of view and a second sensor 324. Herein, the first angle of view of the first lens 312 may be equal to the second angle of view of the second lens 322. The first sensor 314 of the first light detector 310 may detect incident light from the first lens 312 and convert the same into an electrical detection signal, and the second sensor 324 of the second light detector 320 may detect incident light from the second lens 322 and convert the same into an electrical detection signal.

The first light detector 310 may be disposed at a first distance d11 from the central axis 220 of light 210 emitted from the light emitter 200, and the second light detector 320 may be disposed at a second distance d12 from the central axis 220 of light 210 emitted from the light emitter 200. The first distance d11 may be different from the second distance d12. Herein, the first distance d11 may be shorter than the second distance d12.

The first detector 310 may be disposed adjacent to the central axis 220 of light 210 emitted from the light emitter 200, and the second detector 320 may be disposed far from the central axis 220 of light 210 emitted from the light emitter 200. This is because the angle of view of the lens of a detector increases as the distance between the detector and the central axis 220 of the light 210 decreases. The first light detector 310 should be disposed adjacent to the central axis 220 of the light 210 such that the first light detector 310 does not partially or fully overlap the path of light from the light emitter 200. If the first light detector 310 is disposed to overlap the path of light, optical noise may be detected, and thus measurement precision and reliability may be lowered.

In addition, the first detector 310 and the second detector 320 may be disposed such that the central axis 316 of the first detector 310 and the central axis 326 of the second detector 320 intersect each other in the light emission region of the flow channel. Herein, the point at which central axis 316 of the first detector 310 and the central axis 326 of the second detector 320 intersect each other may be a point which the central axis 220 of the light 210 emitted from the light emitter 200 crosses in the light emission region of the flow channel.

As the first and second detectors 310 and 320 are disposed to have different light detection ranges, the dust measurement range may be widened, and dust ranging from low-concentration dust to high-concentration dust may be precisely and accurately measured.

As shown in FIG. 7, the first and second detectors 310 and 320 may be disposed at one side of the central axis 220 of light 210 emitted from the light emitter 200.

The first detector 310 may be disposed such that the central axis 316 of the first detector 310 and the central axis 220 of light 210 emitted from the light emitter 200 form a first angle θ11 therebetween, and the second detector 320 may be disposed such that the central axis 326 of the second detector 320 and the central axis 220 of light 210 emitted from the light emitter 200 form a second angle θ12 therebetween. Herein, the first angle θ11 may be less than the second angle θ12. Since the emission range of light 210 emitted from the light emitter 200 is widened with increase of the distance from the light emitter 200, efficient light detection may be implemented if the second detector 320, which has a narrower light detection range than the first detector 310, is disposed at a longer distance from the light emitter 200 than the first detector 310. The first angle θ11 and the second angle θ12 may be between, for example, about 45° and about 135°. However, embodiments of the present invention are not limited thereto.

In addition, the first and second detectors 310 and 320 may be disposed such that the central axis 316 of the first light detector 310 and the central axis 326 of the second light detector 320 form a third angle θ13 which is an acute angle. If the third angle θ13 between the central axis 316 of the first light detector 310 and the central axis 326 of the second light detector 320 is greater than the acute angle, the space for arrangement of the first and second detectors 310 and 320 may become large and improper to implement compact design of the apparatus.

Accordingly, the first light detector 310 having a wide light detection range is preferably disposed adjacent to the light emitter 200, and the second light detector 320 having a narrow light detection range is preferably disposed far from the light emitter 200.

The first and second detectors 310 and 320 may be positioned in the same plane as the light emitter 200, or may be positioned in a plane different from the plane in which the light emitter 200 is positioned.

As such, according to an embodiment of the present invention, the first and second detectors 310 and 320 may be disposed in various ways to reduce the space for arrangement thereof.

As shown in FIG. 8, the first light detector 310 may be disposed at one side of the central axis 220 of light 210 emitted from the light emitter 200, and the second detector 320 may be disposed at the opposite side of the central axis 220 of light 210 emitted from the light emitter 200. Herein, the first and second detectors 310 and 320 may be disposed symmetrically with respect to the central axis 220 of light 210 emitted from the light emitter 200.

In addition, the first detector 310 may be disposed such that the central axis 316 of the first detector 310 and the central axis 220 of light 210 emitted from the light emitter 200 form a first angle θ11 therebetween, and the second detector 320 may be disposed such that the central axis 326 of the second detector 320 and the central axis 220 of light 210 emitted from the light emitter 200 form a second angle θ12 therebetween. Herein, the first angle θ11 may be equal to the second angle θ12. The first angle θ11 and the second angle θ12 may be between, for example, about 45° and about 135°. However, embodiments of the present invention are not limited thereto.

If the first and second detectors 310 and 320 are symmetrically disposed as described above, the space for arrangement of the first and second detectors 310 and 320 becomes large, and thus does not overlap the path of light emitted from the light emitter 200. Accordingly, optical noise may not be detected and, thus measurement precision and reliability may be improved.

The first and second detectors 310 and 320 may be disposed such that the central axis 316 of the first light detector 310 and the central axis 326 of the second light detector 320 form a third angle θ13, which is an obtuse angle, therebetween. If the third angle θ13 between the central axis 316 of the first light detector 310 and the central axis 326 of the second light detector 320 is less than the obtuse angle, the first and second detectors 310 and 320 may partially or fully overlap the path of light from the light emitter 200, and thus optical noise may be detected. Thereby, measurement precision and reliability may be lowered.

The first and second detectors 310 and 320 may be positioned in the same plane as the light emitter 200, or may be positioned in a plane different from the plane in which the light emitter 200 is positioned.

As such, according to embodiments of the present invention, the first and second detectors 310 and 320 may be disposed in various ways such that optical noise is not detected.

As described above, by adjusting the distance between the optical axis of the light emitter and the detector, the light detection range of the detector may be easily and conveniently determined.

Figure 9:
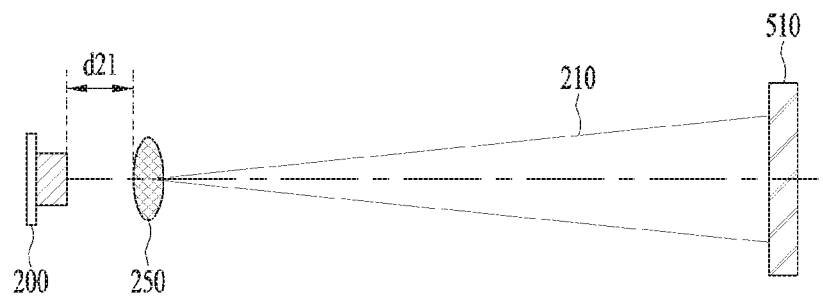
FIGS. 9 to 11 illustrate arrangement of a light absorber.
Figure 10:
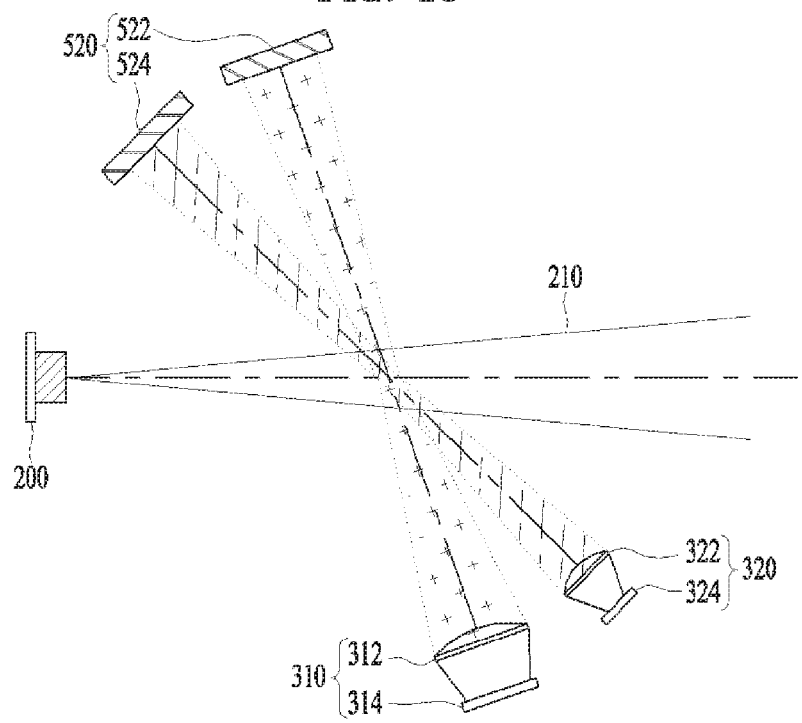
Figure 11:
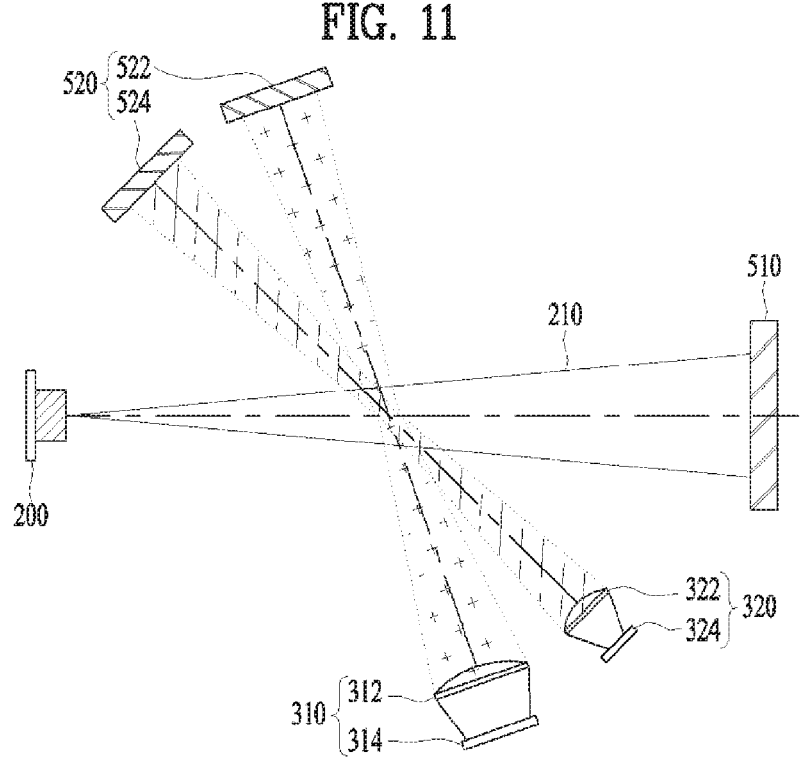

FIGS. 9 to 11 illustrate arrangement of a light absorber.

As shown in FIGS. 9 to 11, a light emitter 200 and a light detector 300 may be provided. Herein, the light detector 300 may include a first detector 310 for detecting light scattered within a first detection range in the light emission region of a flow channel and a second detector 320 for detecting light scattered within a second detection range narrower than the first detection range in the light emission region of the flow channel.

In addition, the first detector 310 may include a first lens 312 having a first angle of view and a first sensor 314, and the second detector 320 may include a second lens 322 having a second angle of view which is narrower than the first angle of view and a second sensor 324. Herein, the first sensor 314 of the first light detector 310 may detect incident light from the first lens 312 and convert the same into an electrical detection signal, and the second sensor 324 of the second light detector 320 may detect incident light from the second lens 322 and convert the same into an electrical detection signal.

As shown in FIG. 9, the light emitter 200 may include a diffusion lens 250 for diffusing light. The diffusion lens 250 may be disposed at a certain distance d21 from the light source of the light emitter 200. In one embodiment, the diffusion lens 250 may be integrated with the light emitter 200 in such a manner that the diffusion lens 250 contacts the light source. Thereby, loss of light emitted from the light source may be reduced.

The diffusion lens to the light emitter 200 serves to diffuse light to allow multiple light detectors having different light detection ranges to accurately detect light.

Further, the light emitter 200 may include a light absorber 510 oriented in the direction of emission of light. Herein, the light absorber 510 may be disposed to face the light emitter 200, and absorb light emitted from the light emitter 200.

The reason for disposing the light absorber 510 as above is that reflected light produced by emission of light 210 from the light emitter 200 and reflection of the light 210 in the apparatus may function as noise in the light detector, lowering reliability of a detection signal of the light detector.

As shown in FIG. 10, the first and second detectors 310 and 320 may include a light absorber 520 disposed to face the detectors. Herein, the light absorber 520 may be disposed to face a corresponding detector with respect to the central axis 220 of light 210 emitted from the light emitter 200, and absorb light scattered by the dust in the flow channel. The light absorber 520 may be disposed to establish one-to-one correspondence with multiple detectors. For example, a first light absorber 522 may be disposed to face the first light detector 310, and a second light absorber 524 may be disposed to face the second light detector 320.

This is because the light scattered by the dust may function as noise in the detectors, lowering reliability of detection signals of the detectors.

As shown in FIG. 11, the light absorber 510 may be disposed to face the light emitter 200, and absorb light emitted from the light emitter 200. In addition, the light absorber 520 may be disposed to face a corresponding detector with respect to the central axis 220 of the light 210 emitted from the light emitter 200, and absorb light scattered by the dust in the flow channel.

As the light absorber 520 is disposed at the opposite side of the light emitter 200 and the first and second detectors 310 and 320, optical noise may be minimized, and precision and reliability of dust measurement may be improved.

Figure 12:
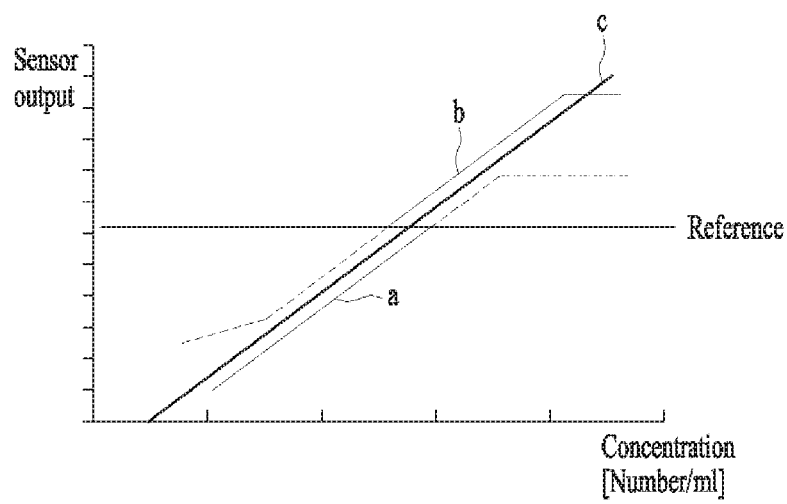
FIGS. 12 to 14 illustrate a method for compensating for an offset of a detection signal.
Figure 13:
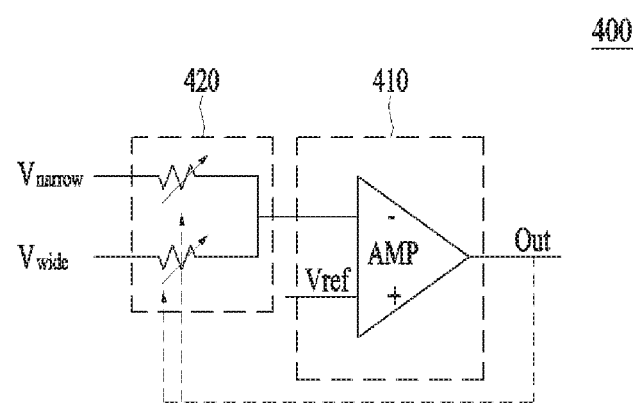
Figure 14:
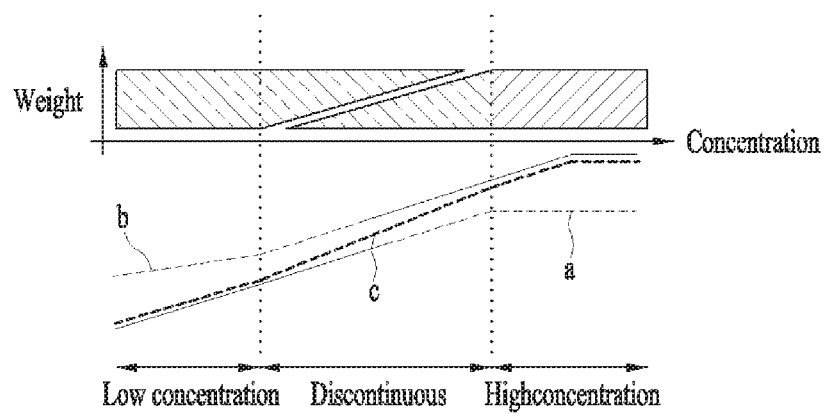

FIGS. 12 to 14 illustrate a method for compensating for an offset of a detection signal.

FIG. 12 is a graph depicting detection signal strength according to dust concentration, FIG. 13 illustrates a circuit for compensating for an offset of detection signals, and FIG. 14 illustrates a method for compensating for an offset in a discontinuous section.

As shown in FIG. 12, a discontinuous section is generated at a reference point for a detection signal a measured by a first detector having a wider detection range and a detection signal b measured by a second detector having a narrow detection range.

Accordingly, according to an embodiment, a compensated signal c may be obtained by compensating for an offset for the detection signals generated in the discontinuous section.

For example, according to an embodiment, the controller may receive detection signals from multiple detectors, compensate for an offset for the received detection signals, and measure dust concentration based on a compensated detection signal.

In compensating for the offset for the received detection signals, the controller may calculate an offset by comparing the detection signals with a predetermined reference value, and compensate for the offset of the detection signals based on the calculated offset.

As shown in FIG. 13, the controller may include an offset compensator 400 for compensating for the offset for the received detection signals.

The offset compensator 400 may include a calculator 410 for calculating an offset value by comparing the detection values received from multiple light detectors with a predetermined reference value and a compensator for compensating for the offset of the detection values based on the calculated offset value and outputting a compensated detection value to the calculator.

Accordingly, the controller may receive detection signals from multiple detectors, compensate for an offset for the detection signals, and measure a dust concentration based on a compensated detection signal. In compensating for the offset for the received detection signals, the controller may calculate an offset by comparing the detection signals received from multiple light detectors with a predetermined reference value, and compensate for the offset of the detection signals based on the calculated offset.

As shown in FIG. 14, the controller according to an embodiment of the present invention may divide the detection signals into a low-concentration section, a discontinuous section and a high-concentration section according to dust concentrations. The controller may consider, in the low-concentration section, a first detection signal a received from a detector having a first light detection range. The controller may consider, in the high-concentration section, a second detection signal b received from a detector having a second light detection range, which is narrower than the first light detection range. In the discontinuous section, the controller may consider a third detection signal c, for which the weight of the first detection signal a is increased and the weight of the second detection signal b is decreased as a concentration point moves toward the low-concentration section, while the weight of the first detection signal a is decreased and the weight of the second detection signal b is increased as a concentration point moves toward the high-concentration section.

As another example, in compensating for the offset for the received detection signals, the controller may divide the detection signals into a low-concentration section, a discontinuous section and a high-concentration section according to dust concentrations. In the low-concentration section, the offset of the detection signals may be compensated for according to Equation 1 below. In the high-concentration section, the offset of the detection signals may be compensated for according to Equation 2 below. In the discontinuous section, the offset of the detection signals may be compensated for according to Equation 3 below.

$Co=Cw$ (wherein Co denotes a compensated detection signal, and Cw denotes the first detection signal received from a detector having a wide light detection range)  Equation 1

$Co=Cn$ (wherein Co denotes a compensated detection signal, and Cn denotes the second detection signal received from a detector having a narrow light detection range)  Equation 2

$Wn=\text{Update}Wn(Co)$ $Co=Cn*Wn+Cw*(1-Wn)$  Equation 3

(wherein Wn denotes a weight (between 0 and 1) of the second detection signal received from a detector having a narrow light detection range)

As another example, in compensating for the offset for the received detection signals, the controller may calculate an offset by comparing the detection signals with a predetermined reference value, and perform primary compensation for the offset of the detection signals based on the calculated offset. Then, the controller may divide the detection signals for which the primary compensation for the offset has been performed into a low-concentration section, a discontinuous section and a high-concentration section according to dust concentrations. The controller may consider, in the low-concentration section, a first detection signal received from a detector having a first light detection range, and consider, in the high-concentration section, a second detection signal received from a detector having a second light detection range, which is narrower than the first light detection range.

In the discontinuous section, the controller may consider a third detection signal obtained by differently adjusting the weight of the first detection signal according to the subsections. Thereby, the controller may perform secondary compensation for the offset of the detection signals Herein, in the discontinuous section, the third detection signal may increase the weight of the first detection signal and decrease the weight of the second detection signal as a concentration point moves toward the low-concentration section, while decreasing the weight of the first detection signal and increasing the weight of the second detection signal as a concentration point moves toward the high-concentration section.

As described above, an offset may be calculated by comparing detection signals with a predetermined reference value, and the offset of the detection signals may be easily and simply compensated for based on the calculated offset.

In addition, according to an embodiment of the present invention, detection signals may be divided into a low-concentration section, a discontinuous section and a high-concentration section according to dust concentrations and the offset of the detection signals is compensated for by adjusting weights for some of the detection signals according to the sections. Accordingly, reliability of compensation may be enhanced.

FIGS. 15 to 18 are flowcharts illustrating a method for measuring dust for a dust measuring apparatus according to an embodiment of the present invention.

Figure 15:
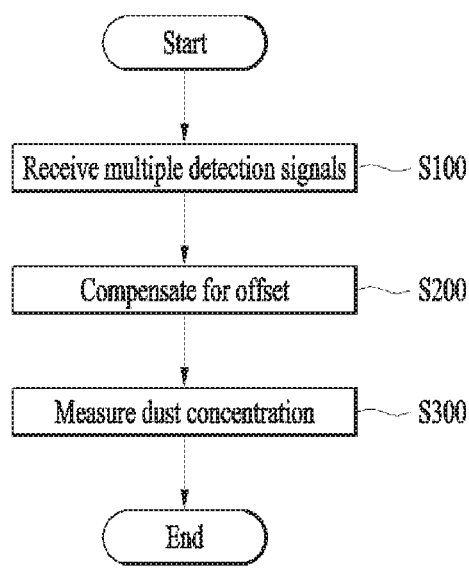
FIGS. 15 to 18 are flowcharts illustrating a method for measuring dust for a dust measuring apparatus according to an embodiment of the present invention.

As shown in FIG. 15, the controller according to an embodiment of the present invention controls a flow channel defining unit to define a flow channel through which a fluid containing dust moves.

In addition, the controller controls the light emitter to emit light into the flow channel.

Subsequently, the controller controls the light detector to detect light scattered by the dust in the flow channel and converts the same into an electrical detection signal.

Next, the controller receives detection signals from multiple detectors having different light detection ranges (S100).

Then, the controller compensates for an offset for the received detection signals (S200).

Subsequently, the controller may measure a dust concentration based on a compensated detection signal.

Figure 16:
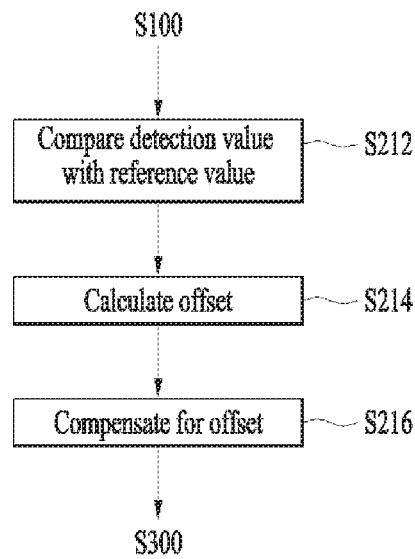

As shown in FIG. 16, in step S200 of compensating for the offset for the received detecting signals, upon receiving the detection signals from the multiple detectors having different light detection ranges, the controller compares detection values received from the multiple light detectors with a predetermined reference value (S212), and calculate an offset value (S213). Then, the controller may compensate for the offset for the detection signals based on the calculated offset value (S216).

Figure 17:
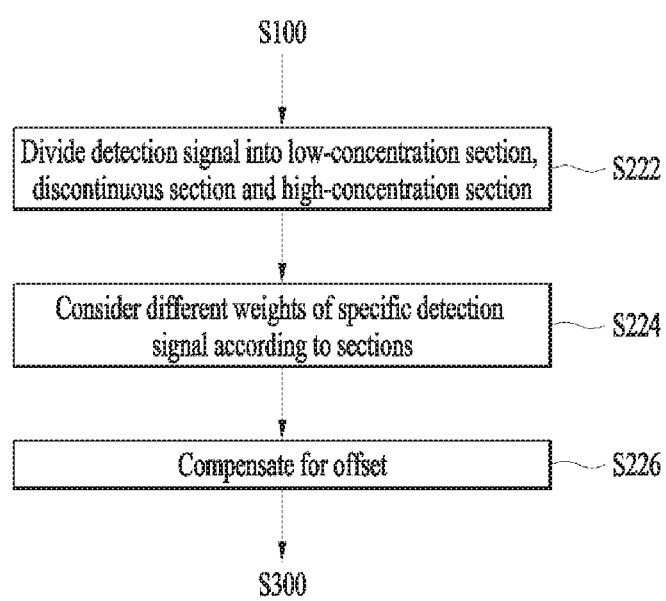

As another example, as shown in FIG. 17, in step S200 of compensating for the offset for the received detection signals, upon receiving the detection signals from the multiple detectors having different light detection ranges, the controller divides the detection signals into a low-concentration section, a discontinuous section and a high-concentration section according to dust concentrations (S222). The controller considers, in the low-concentration section, a first detection signal received from a detector having a first light detection range, considers, in the high-concentration section, a second detection signal received from a detector having a second light detection range narrower than the first light detection range, and considers, in the discontinuous section, a third detection signal obtained by differently adjusting the weight of the first detection signal according to sub-sections (S224). Then, the controller compensates for an offset of the detection signals based on the considered detection signals (S226). For the third detection signal, the weight of the first detection signal is increased and the weight of the second detection signal is decreased as a concentration point moves toward the low-concentration section in the discontinuous section, while the weight of the first detection signal is decreased and the weight of the second detection signal is increased as a concentration point moves toward the high-concentration section in the discontinuous section.

In one embodiment, in the low-concentration section, the offset of the detection signals may be compensated for according to Equation 1 below. In the high-concentration section, the offset of the detection signals may be compensated for according to Equation 2 below. In the discontinuous section, the offset of the detection signals may be compensated for according to Equation 3 below.

$$Co = Cw \text{ (wherein Co denotes a compensated detection signal, and Cw denotes the first detection signal received from a detector having a wide light detection range)} \quad \text{Equation 1}$$

$$Co = Cn \text{ (wherein Co denotes a compensated detection signal, and Cn denotes the second detection signal received from a detector having a narrow light detection range)} \quad \text{Equation 2}$$

$$Wn = \text{Update } Wn(Co)$$

$$Co = Cn*Wn + Cw*(1-Wn) \quad \text{Equation 3}$$

(wherein Wn denotes a weight (between 0 and 1) of the second detection signal received from a detector having a narrow light detection range)

Figure 18:
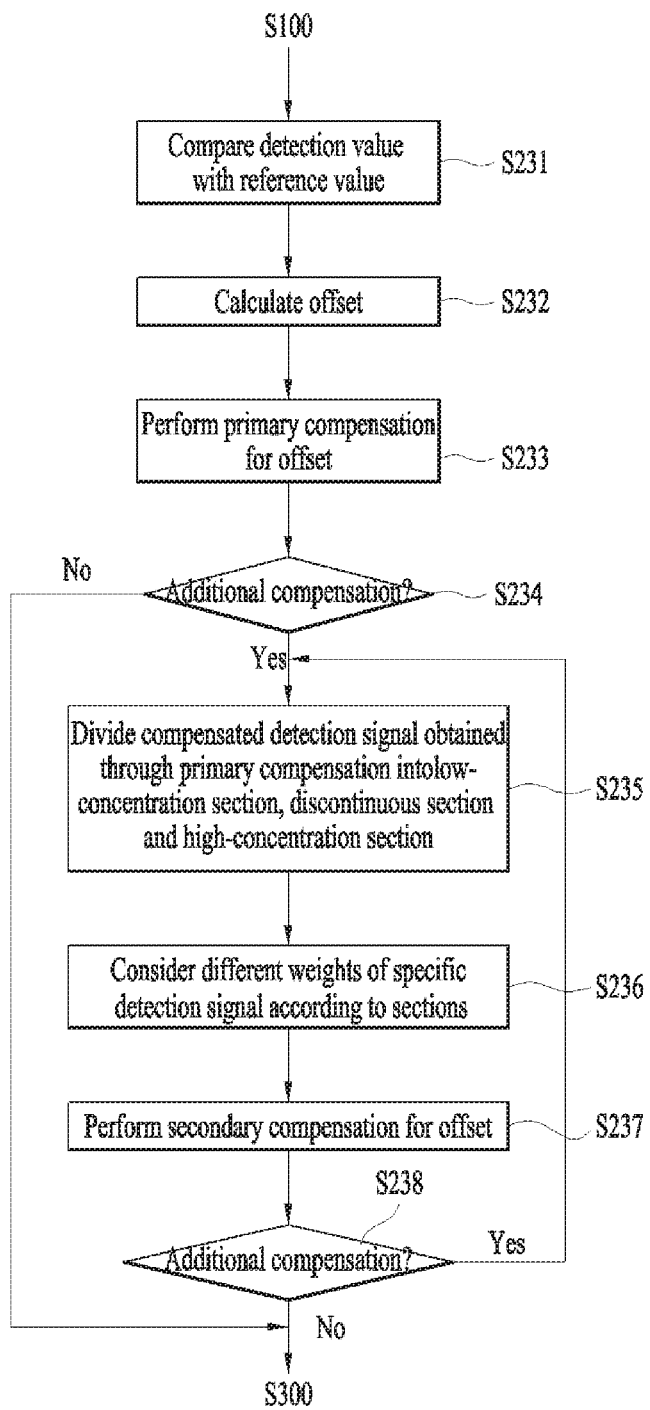

As another example, as shown in FIG. 18, in step S200 of compensating for the offset for the received detection signals, upon receiving the detection signals from the multiple detectors having different light detection ranges, the controller compares the detection values received from the multiple light detectors with a predetermined reference value (S231), and calculates an offset value (S232). Then, the controller may perform primary compensation for the offset of the detection signals based on the calculated offset (S233). Subsequently, the controller checks if there is any additional compensation request (S234). If there is an additional compensation request, the controller divides the detection signals for which the primary compensation for the offset has been performed into a low-concentration section, a discontinuous section and a high-concentration section according to dust concentrations (S235). Then, the controller considers, in the low-concentration section, a first detection signal received from a detector having a first light detection range, and considers, in the high-concentration section, a second detection signal received from a detector having a second light detection range narrower than the first light detection range, and considers, in the discontinuous section, a third detection signal obtained by differently adjusting the weight of the first detection signal according to the subsections (S236). Then, the controller performs secondary compensation for the offset of the detection signals based on the considered detection signals (S237). Subsequently, the controller checks if there is any additional compensation request (S238). If there is an additional compensation request, the controller may repeat step S235. Herein, in the discontinuous section, the third detection signal may increase the weight of the first detection signal and decrease the weight of the second detection signal as a concentration point moves toward the low-concentration section, while decreasing the weight of the first detection signal and increasing the weight of the second detection signal as a concentration point moves toward the high-concentration section.

By repeating offset compensation as described above, errors of detection signals in the discontinuous section may be reduced. Thereby, precision and reliability of dust measurement may be enhanced, and dust measurement within a wide detection range from a low concentration to a high concentration may be implemented.

As described above, with the present invention, the dust measurement range may be widened using multiple detectors having a different light detection ranges.

In addition, measurement precision may be enhanced in a wide measurement range by compensating for the offset for detection signals received from multiple detectors.

In addition, since the light detection ranges of the detectors are determined using lenses having different angles of view, a simple and low-cost design may be implemented.

In addition, according to an embodiment of the present invention, the overall size of the apparatus may be reduced through efficient spatial arrangement, by arranging a detector having a wider measurement range adjacent to the light emitter.

Further, the detectors may be disposed such that the central axes of the detectors intersect each other in the light emission region of the flow channel. Thereby, precision of dust measurement may be enhanced.

In addition, according to an embodiment of the present invention, by adjusting the distance between the optical axis of the light emitter and the detector, the light detection range of the detector may be easily and conveniently determined.

In addition, according to an embodiment of the present invention, as a light absorber is disposed in a region facing a light emitter or detector, optical noise may be reduced.

In addition, according to an embodiment of the present invention, an offset may be calculated by comparing detection signals with a predetermined reference value, and the offset of detection signals may be easily and simply compensated for based on the calculated offset.

Further, according to an embodiment of the present invention, detection signals are divided into a low-concentration section, a discontinuous section and a high-concentration section according to dust concentrations and the offset of the detection signals is compensated for by adjusting weights for some of the detection signals according to the sections. Accordingly, reliability of compensation may be enhanced.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An apparatus for measuring dust, comprising:
   a flow channel unit for defining a flow channel allowing a fluid containing dust to move through;
   a light emitter for emitting light into the flow channel;
   a light detector for detecting light scattered from the dust in the flow channel and converting the detected light scattered from the dust in the flow channel into an electrical detection signal, the light detector comprising a plurality of detectors having different light detection ranges; and
   a controller for controlling the flow channel unit, the light emitter and the light detector,
   wherein the controller is configured to:
   receive detection signals from the plurality of detectors;
   compensate for an offset for the received detection signals: and
   measure a dust concentration based on the compensated detection signals,
   wherein, when the controller compensates for the offset for the received detection signals, the controller is further configured to:
   divide the detection signals into a low-concentration section, a discontinuous section and a high-concentration section according to dust concentrations;
   apply, in the low-concentration section, a first detection signal received from a detector having a first light detection range;
   apply, in the high-concentration section, a second detection signal received from a detector having a second light detection range, the second light detection range being narrower than the first light detection range; and
   apply a third detection signal in the discontinuous section, the third detection signal being obtained by increasing a weight of the first detection signal and decreasing a weight of the second detection signal as a concentration point moves toward the low-concentration section and by decreasing the weight of the first detection signal and increasing the weight of the second detection signal as the concentration point moves toward the high-concentration section.

2. The apparatus according to claim 1, wherein the light detector comprises:
   a first detector for detecting light scattered within a first detection range in a light emission region of the flow channel; and
   a second detector for detecting light scattered within a second detection range in the light emission region of the flow channel, the second detection range being narrower than the first detection range.

3. The apparatus according to claim 2, wherein the first detector comprises a first lens having a first angle of view, wherein the second detector comprises a second lens having a second angle of view, and wherein the second angle of view being narrower than the first angle of view.

4. The apparatus according to claim 3, wherein the first detector is disposed at a first distance from a central axis of the light emitted from the light emitter,
   the second detector is disposed at a second distance from the central axis of the light emitted from the light emitter, and
   wherein the first distance is equal to the second distance.

5. The apparatus according to claim 3, wherein the first detector and the second detector are disposed such that a central axis of the first detector and a central axis of the second detector intersects with each other in the light emission region of the flow channel.

6. The apparatus according to claim 5, wherein a point of intersection between the central axis of the first detector and the central axis of the second detector is crossed by a central axis of the light emitted from the light emitter in the light emission region of the flow channel.

7. The apparatus according to claim 3, wherein the first and second detectors are disposed at one side of a central axis of the light emitted from the light emitter.

8. The apparatus according to claim 7, wherein the first detector is disposed such that a central axis of the first detector and the central axis of the light emitted from the light emitter form a first angle therebetween,
wherein the second detector is disposed such that a central axis of the second detector and the central axis of the light emitted from the light emitter form a second angle in between, and
wherein the first angle is less than the second angle.

9. The apparatus according to claim 3, wherein the first detector is disposed at one side of a central axis of the light emitted from the light emitter, and
the second detector is disposed at an opposite side of the central axis of the light emitted from the light emitter.

10. The apparatus according to claim 9, wherein
the first and second detectors are disposed symmetrically with respect to the central axis of the light emitted from the light emitter.

11. The apparatus according to claim 9, wherein
the first detector is disposed such that a central axis of the first detector and the central axis of the light emitted from the light emitter form a first angle in between,
wherein the second detector is disposed such that a central axis of the second detector and the central axis of the light emitted from the light emitter form a second angle in between,
wherein the first angle is equal to the second angle.

12. The apparatus according to claim 1, wherein the controller comprises:
an offset compensator for compensate for the offset for the received detection signals,
wherein the offset compensator comprises:
a calculator for calculating an offset value by comparing detection values received from the detectors with a predetermined reference value, and
a compensator for compensating for an offset of the detection values based on the calculated offset value and outputting a compensated detection value to the calculator.

13. The apparatus according to claim 1, wherein, when the controller compensates for the offset for the received detection signals, the controller is further configured to:
calculate an offset by comparing the detection signals with a predetermined reference value and perform primary compensation for the offset of the detection signals based on the calculated offset, and
divide the detection signals subjected to the primary compensation for the offset into a low-concentration section, a discontinuous section and a high-concentration section according to dust concentrations and perform secondary compensation for the offset by:
applying, in the low-concentration section, a first detection signal received from a detector having a first light detection range;
applying, in the high-concentration section, a second detection signal received from a detector having a second light detection range, the second light detection range being narrower than the first light detection range; and
applying a third detection signal in the discontinuous section, the third detection signal being obtained by differently adjusting a weight of the first detection signal according to sub-sections of the discontinuous section.

14. The apparatus according to claim 13, wherein the third detection signal is obtained by:
increasing the weight of the first detection signal and decreasing a weight of the second detection signal as a concentration point moves toward the low-concentration section in the discontinuous section, and
decreasing the weight of the first detection signal and increasing the weight of the second detection signal as the concentration point moves toward the high-concentration section in the discontinuous section.

15. A method for measuring dust in an apparatus for measuring the dust comprising a plurality of detectors having different light detection ranges, the method comprising:
receiving detection signals from the detectors;
compensating for an offset for the received detection signals; and
measuring a dust concentration based on the compensated detection signals
wherein the compensating for the offset comprises:
dividing the detection signals into a low-concentration section, a discontinuous section and a high-concentration section according to dust concentrations, and
compensating for the offset of the detection signals by:
applying, in the low-concentration section, a first detection signal received from a detector having a first light detection range;
applying, in the high-concentration section, a second detection signal received from a detector having a second light detection range, the second light detection range being narrower than the first light detection range; and
applying a third detection signal in the discontinuous section, the third detection signal being obtained by differently adjusting a weight of the first detection signal according to sub-sections of the discontinuous section.

16. The method according to claim 15, wherein the compensating for the offset comprises:
calculating an offset value by comparing detection values received from the detectors with a predetermined reference value; and
compensating for the offset of the detection signals based on the calculated offset value.

17. The method according to claim 15, wherein the third detection signal is obtained by:
increasing the weight of the first detection signal and decreasing a weight of the second detection signal as a concentration point moves toward the low-concentration section in the discontinuous section, and
decreasing the weight of the first detection signal and increasing the weight of the second detection signal as the concentration point moves toward the high-concentration section in the discontinuous section.

18. The method according to claim 15, wherein the compensating for the offset comprises:
calculating an offset by comparing the detection signals with a predetermined reference value and performing primary compensation for the offset of the detection signals based on the calculated offset, and dividing the detection signals subjected to the primary compensation for the offset into a low-concentration section, a discontinuous section and a high-concentration section according to dust concentrations and performing secondary compensation for the offset by:

applying, in the low-concentration section, a first detection signal received from a detector having a first light detection range, applying, in the high-concentration section, a second detection signal received from a detector having a second light detection range, the second light detection range being narrower than the first light detection range, and applying a third detection signal in the discontinuous section, the third detection signal being obtained by differently adjusting a weight of the first detection signal according to sub-sections of the discontinuous section.

* * * * *